US006514504B1

(12) United States Patent
Yen et al.

(10) Patent No.: US 6,514,504 B1
(45) Date of Patent: *Feb. 4, 2003

(54) DISCONTINUOUS FILMS FROM SKIN CARE COMPOSITIONS

(75) Inventors: Helen Shu Ying Yen, Cockeysville; Thomas Elliot Rabe; Jeffrey Keith Leppla, both of Baltimore, all of MD (US); Robert Lawrence Prosise, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/628,631

(22) Filed: Jul. 31, 2000

Related U.S. Application Data

(63) Continuation-in-part of application No. 09/583,616, filed on May 31, 2000.
(60) Provisional application No. 60/149,586, filed on Aug. 18, 1999.

(51) Int. Cl.[7] ........................... A61K 7/021; A61K 7/00; A61K 7/02; A61K 9/14; A61K 9/16
(52) U.S. Cl. ..................... 424/401; 424/484; 424/485; 424/486; 424/490; 424/501; 424/63
(58) Field of Search ................ 424/401, 484, 485, 486, 490, 501, 63, 78.03

(56) References Cited

U.S. PATENT DOCUMENTS

| | | | |
|---|---|---|---|
| 3,012,969 A | 12/1961 | van der Minne et al. | 252/153 |
| 4,079,894 A | 3/1978 | Harjar et al. | 239/526 |
| 4,122,845 A | 10/1978 | Stouffer et al. | 128/66 |
| 4,143,819 A | 3/1979 | Hastings | 239/707 |
| 4,194,696 A | 3/1980 | Harjar | 239/707 |
| 4,258,073 A | 3/1981 | Payne | 427/1 |
| 4,776,515 A | 10/1988 | Michalchik | 239/3 |
| 5,200,248 A | 4/1993 | Thompson et al. | 428/131 |
| 5,222,663 A | 6/1993 | Noakes et al. | 239/3 |
| 5,229,105 A | 7/1993 | Wilmsmann | 424/59 |
| 5,268,166 A | 12/1993 | Barnett et al. | 424/47 |
| 5,296,681 A | 3/1994 | Tschauder | 219/410 |
| 5,322,684 A | 6/1994 | Barnett et al. | 424/47 |
| 5,422,630 A | 6/1995 | Quinn et al. | 340/661 |
| 5,468,488 A | 11/1995 | Wahl | 424/78.03 |
| 5,494,674 A | 2/1996 | Barnett et al. | 424/401 |
| 5,505,937 A | 4/1996 | Castrogiovanni et al. | 424/64 |
| 5,519,159 A | 5/1996 | Narabe et al. | 558/169 |
| 5,662,890 A | 9/1997 | Punto et al. | 424/59 |
| 5,674,481 A | 10/1997 | Wahi | 424/78.03 |
| 5,683,706 A * | 11/1997 | LaFleur et al. | 424/401 |
| 5,800,816 A | 9/1998 | Brieva et al. | 424/63 |
| 5,945,111 A | 8/1999 | Esser | 424/401 |

FOREIGN PATENT DOCUMENTS

| | | | |
|---|---|---|---|
| BE | 882449 | 7/1980 | |
| BE | 882450 | 7/1980 | |
| EP | 0 096 731 | 12/1983 | A61N/1/04 |
| EP | 0 523 960 | 1/1993 | B05D/1/04 |
| EP | 0 523 961 | 1/1993 | B05D/1/04 |
| EP | 0 523 962 | 1/1993 | B01D/1/04 |
| EP | 0 523 963 | 1/1993 | B05D/1/04 |
| EP | 0 523 964 | 1/1993 | B05D/1/04 |
| EP | 0 544 158 | 6/1993 | C08F/26/06 |
| FR | 2127433 | 10/1972 | |
| GB | 2 128 900 | 5/1984 | B05B/5/06 |
| GB | 2 273 673 | 6/1994 | B05B/5/025 |
| GB | 2 273 872 | 7/1994 | B05B/5/025 |
| GB | 2 291 804 A | 2/1996 | |
| GB | 2 319 177 | 5/1998 | |
| JP | 56-097214 | 8/1981 | A61K/7/13 |
| JP | 7-60166 | 3/1995 | B05B/5/025 |
| JP | 10-146216 | 6/1998 | A45D/33/38 |
| SU | 867 927 | 9/1981 | C14B/1/54 |
| WO | WO 94/11119 | 5/1994 | B05D/1/04 |
| WO | WO 94/27560 | 12/1994 | A61K/7/02 |
| WO | WO 95/29758 | 11/1995 | B05B/5/025 |
| WO | WO 96/03964 A1 | 2/1996 | |
| WO | WO 96/10459 | 4/1996 | B05B/5/057 |
| WO | WO 96/11062 | 4/1996 | B05B/5/053 |
| WO | WO 97/04737 A1 | 2/1997 | |
| WO | WO 97/17057 A1 | 5/1997 | |
| WO | WO-97/17058 A1 * | 5/1997 | A61K/7/48 |
| WO | WO 97/33527 | 9/1997 | A61B/19/00 |
| WO | WO 98/26752 A1 | 6/1998 | |

OTHER PUBLICATIONS

Cook, T.H., et al., "Topographics of Dry Skin, Non–dry Skin, and Cosmetically Treated Dry Skin as Quantified by Skin Profilometry", J. Soc. Cosmet. Chem., vol. 36, pp. 143–152 (Mar./Apr. 1985).

Dorogi, P.L., et al., "Assessment of Skin Conditions Using Profilometry", Cosmetics & Toiletries, vol. 104, pp. 39–44 (Mar. 1989).

U.S. application No. 09/629,734, Rabe et al., filed Jul. 31, 2000.

U.S. application No. 09/629,765, Rabe et al., filed Jul. 31, 2000.

U.S. application No. 09/628,630, Rabe et al., filed Jul. 31, 2000.

* cited by examiner

*Primary Examiner*—Frederick Krass
*Assistant Examiner*—Clinton Ostrup
(74) *Attorney, Agent, or Firm*—Dara M. Kendall; Tara M. Rosnell; Steven W. Miller

(57) ABSTRACT

The present invention relates to substantially uniform, discontinuous films of a skin care product having a defined average particle size, particle spacing and coverage value. The films provide improved skin appearance, e.g., good apparent coverage and a natural look. The films can be formed by any method which provides the defined particle size, particle spacing and coverage value, including silk screening and the like and electrostatic spray techniques. The films are preferably formed by electrostatically spraying the composition onto the skin.

12 Claims, No Drawings

DISCONTINUOUS FILMS FROM SKIN CARE COMPOSITIONS

CROSS REFERENCE TO RELATED APPLICATION

This application claims priority under Title 35, United States Code 119(e) from U.S. Provisional Application No. 60/149,586, filed on Aug. 18, 1999 and is a continuation-in-part application of U.S. Application Ser. No. 09/583,616, filed May 31, 2000.

FIELD OF THE INVENTION

The present invention relates to discontinuous films formed from skin care compositions which are preferably electrostatically sprayed. The films are characterized by a particular particle size, particle spacing and coverage value which have been found to provide improved appearance and/or skin feel.

BACKGROUND OF THE INVENTION

A variety of topically-applied skin treatment products, including skin lotions, creams, cosmetic foundations and the like, are known. Such products are generally applied by massaging or rubbing into the skin with the fingers or sponge-type applicator to provide essentially complete coverage of the skin with the product. Typically, about 80% or more of the skin surface is covered by the product, forming an essentially continuous film of product on the skin. While such continuous coverage can be beneficial, in certain applications it can result in undesirable effects. For example, while it is desirable to provide cosmetic foundations having good coverage properties, it has been difficult to achieve good coverage while maintaining a natural look and/or skin feel.

Other methods of applying topical products are also known, including air brush, aerosol spraying, non-aerosol pump spraying, and electrostatic spraying. For example, electrostatic spraying of skin treatment agents is disclosed in U.S. Pat. No. 5,494,674, issued to Barnett et al. on Feb. 27, 1996. Electrostatic spraying of topical materials has been proposed as a means for more efficient consumption and product activity, control over application, ease and cleanliness/hygiene of application, and even coverage.

While a variety of topical compositions have been provided, there is an ongoing need to provide skin care compositions which impart good coverage yet a natural appearance. Furthermore, there is an ongoing need to improve the feel of topically applied compositions, e.g., to reduce the sensations of tightness, stiffness, tackiness and/or dryness which can result from some topical products, particularly long wear or transfer resistant products.

In view of these limitations, after much experimentation it has now been found that substantially uniform and discontinuous films formed from topical compositions comprising particulates and having defined physical properties provide improved appearance. More particularly, films of the present invention have defined particle sizes, particle spacing and coverage values according to the methods herein.

The films exhibit an actual percent skin coverage which is significantly lower than products which are not applied in a discontinuous film, but rather for example are applied using conventional methods of massaging or rubbing into the skin. Surprisingly, the films nonetheless provide good coverage in terms of appearance, e.g., evening skin tone and masking local skin imperfections such as spots, blemishes, circles and the like. Furthermore, since a significantly high percentage of the user's bare skin is integrated into the overall appearance of the product application, the appearance is more natural. The actual percent skin coverage of the films is defined herein in terms of their coverage value.

Further appearance benefits have been surprisingly realized where the film is formed from a topical composition comprising an emulsion having the particulate material dispersed in the continuous external phase and are substantially, preferably essentially not present in the internal phase. When such products are applied to the skin, a "clustering" phenomena of pigments results which makes the apparent particle size smaller than the actual particle size which is applied. Such smaller apparent particle sizes tend to provide improved skin appearance such as a more natural look.

Because of one or more of the aforementioned properties, it is possible to utilize a broader range of shade palettes while maintaining a natural appearance.

In addition to such appearance improvements, the present invention also tends to improve skin feel, e.g., reduce sensations of tightness, dryness, tackiness and/or stiffness, which might otherwise be experienced if the film were continuous. The present invention also increases formulation capability since it becomes possible to use a wider variety of skin care components which may otherwise have the potential to irritate certain individuals. Application of compositions as a discontinuous film according to the present invention tends to reduce any potential for irritation.

SUMMARY OF THE INVENTION

The present invention relates to substantially uniform, discontinuous films of a topical composition having a defined average particle size, particle spacing and coverage values according the methods described herein. The films provide improved skin appearance, e.g., good apparent coverage and a natural look.

The films hereof have an average particle size (diameter) of from about 0.5 to about 150 microns, more preferably from about 1 to about 100 microns, most preferably from about 5 to about 80 microns. Preferred standard deviations for the average particle size are or are less than 1.5 times, more preferably 1.0 times, most preferably 0.7 times, the average particle size.

The films hereof also have an average spacing between particles of at least about 3 microns, more preferably at least about 7 microns, most preferably at least about 10 microns.

The films further have a coverage value of less than about 80%, preferably less than about 70%, more preferably less than about 60.

The topical compositions from which the films are formed comprise one or more particulate materials dispersed in a carrier which comprises one or more liquid diluents. The liquid diluents may be volatile or nonvolatile, and polar or non-polar.

The composition is preferably electrostatically sprayable, comprising at least one conductive material which is preferably a liquid, more preferably a volatile liquid. The electrostatically sprayable compositions may also comprise one or more insulating materials, at least one of which is preferably liquid and more preferably a volatile liquid. More preferably, the electrostatically sprayable composition comprises an emulsion wherein the insulating material and conductive material are in different phases, even more preferably wherein the insulating material is in the continuous, external phase and the conductive material is in the discontinuous, internal phase.

In a preferred embodiment, the topical composition further comprises one or more materials for imparting transfer or wear resistance, structuring or thickening agents, emulsifiers, co-solubilizers and mixtures thereof.

The films can be formed by topical application of the composition by any suitable method, including silk screening or the like and electrostatic spray techniques, to provide the defined particle size, particle spacing and coverage value. The films are preferably formed by electrostatically spraying the composition onto the skin.

The present invention can be used in a variety of topical applications where deposition of a discontinuous product film would be advantageous, and is particularly well suited to cosmetic foundation applications. For example, compositions of the invention may be designed and utilized to reduce potential for local irritation, to provide more uniform and/or natural-looking application of skin treatment agents or compositions, including pigmented products such as color cosmetics, and/or to improve the feel of extended-wear or transfer resistant products. In particular, extended-wear or transfer resistant products have been found to exhibit improved feel when applied discontinuously in accordance with the present invention. Pigmented products provide sufficient coverage of imperfections, while providing a natural look. Better shade matching of skin and pigmented foundation compositions is also enabled, e.g., because the foundation integrates with the natural skin color, creating a composite shade. The present invention therefore enables broader useful shade palettes.

DETAILED DESCRIPTION OF THE INVENTION

The essential elements of the present invention are herein described below. Also included are non-limiting descriptions of various optional and preferred elements useful in the present invention.

The present invention can comprise, consist of, or consist essentially of any of the required or optional components and/or limitations described herein.

In the description of the invention various embodiments and/or individual features are disclosed. As will be apparent for the skilled practitioner all combinations of such embodiments and features are possible and can result in preferred executions of the invention.

All percentages and ratios are calculated by weight unless otherwise indicated. All percentages are calculated based on the total composition unless otherwise indicated.

All component or composition levels are in reference to the active level of that component or composition, and are exclusive of impurities, for example, residual solvents or by-products, which may be present in commercially available sources.

Referred to herein are trade names for materials. The inventors herein do not intend to be limited by materials under a certain trade name. Equivalent materials (e.g., those obtained from a different source under a different name or catalog (reference) number) to those referenced by trade name may be substituted and utilized in the compositions herein.

The compositions and components thereof herein described are suitable for topical application, that is suitable for use in contact with human skin without undue toxicity, incompatibility, instability, allergic response, and the like within the scope of sound medical judgment.

Active and other ingredients useful herein may be categorized or described herein by their cosmetic, prophylactic and/or therapeutic benefit or their postulated mode of action. It is to be understood that the active and other ingredients useful herein can in some instances provide more than one cosmetic, prophylactic and/or therapeutic benefit or operate via more than one mode of action. Therefore, classifications herein are made for the sake of convenience and are not intended to limit an ingredient to the particularly stated application or applications listed.

All documents referred to herein, including all patents, patent applications, and printed publications, are hereby incorporated by reference in their entirety.

The topical compositions from which the films are formed comprise one or more particulate materials dispersed in a carrier which comprises one or more liquid diluents. The liquid diluents may be volatile or nonvolatile, and polar or non-polar.

The composition is preferably electrostatically sprayable, comprising at least one conductive material which is preferably a liquid, more preferably a volatile liquid. The electrostatically sprayable compositions may also comprise one or more insulating materials, at least one of which is preferably liquid and more preferably a volatile liquid. More preferably, the electrostatically sprayable composition comprises an emulsion wherein the insulating material and conductive material are in different phases, even more preferably wherein the insulating material is in the continuous, external phase and the conductive material is in the discontinuous, internal phase. In a preferred embodiment, the topical composition further comprises one or more materials for imparting transfer or wear resistance, structuring or thickening agents, emulsifiers, co-solubilizers and mixtures thereof.

I. FILM CHARACTERISTICS

In additional to their compositional structure, films of the present invention are characterized by their physical characteristics of average particle size, particle spacing and coverage value.

The films hereof have an average particle size (diameter) of from about 0.5 to about 150 microns, more preferably from about 1 to about 100 microns, most preferably from about 5 to about 80 microns. Preferred standard deviations for the average particle size are or are less than 1.5 times, more preferably 1.0 times, most preferably 0.7 times, the average particle size.

The films hereof also have an average spacing between particles of at least about 3 microns, more preferably at least about 7 microns, most preferably at least about 10 microns.

The films are discontinuous, that is, they provide less than about 80% actual coverage of the substrate to which the topical composition is applied. The films hereof have a coverage value of less than about 80%, preferably less than about 70%, more preferably less than about 60%.

These properties of particle size, particle spacing and coverage value are determined in accordance with the following methods:

(A) Methods Overview

The methods utilize computerized image analysis which measures the distribution of particle sizes, relative spacing and areas in a test film based on the areas of light colored particles on dark backgrounds (using a 0:255 gray scale).

The test film is prepared by applying a composition onto a substrate in the manner desired for topical application and allowing it to dry. A microscope and camera are used to capture an image of the resulting film which is displayed on a computer monitor (framegrabber), and information from the image is inputted to a computer and analyzed utilizing imaging software. The methods involve the steps of:

1. Calibrating the camera brightness/contrast (black/white) to obtain the highest contrast between light and dark.
2. Calibrating the monitor pixels spatially to determine the length of each pixel to be measured.
3. Setting the threshold for the image being analyzed on a gray scale of 0–255.
4. Classifying a given pixel in the image as being substrate or test product film based on the threshold value. Points which have light intensity at or above the threshold are designated foreground (corresponding to test product film); points having a light intensity below the threshold are designated background (corresponding to substrate).
5. Constructing connected components for the foreground areas (computer-drawn lines around the common area designated as test product in step (4), hereinafter alternatively referred to as "particles").
6. Determining the size of the connected components based on the number of pixels. In order to be included in the analyses, the perimeter of a particle must be at least 16 pixels. This method displays and determines the size for all particles found which meet this perimeter requirement.
7. At least 10 random representative sample images are acquired and analyzed for each test product.

The measured distribution data can be displayed as a graph or can be written out to a spreadsheet, including histograms.

Many computer programs for imaging analyses and calculations of the type described herein are commercially available, and can be tailored to perform the functions described herein by those having ordinary skill in the art without undue experimentation.

(B) Equipment/Settings

The following equipment and corresponding settings are utilized.

1. Zeiss SV-11 stereomicroscope with a 1× lens (S1,0×) or the equivalent thereof—Magnification is 5.0 and the iris is completely open ("big dot"). This is a magnification of 5×.
2. Fostec 8375 (EJA) Ring Light (reflected light) or the equivalent thereof, mounted on the microscope lens. Set the ring light to maximum.
3. Computer with frame grabber board (e.g., an Occulus TCX board or the like) to digitize the analog signal of the camera, suitable imaging software (e.g., Optimas 5.21 or higher, commercially available from Media Cybernetics, L.P. of Silver Spring, Md.) and suitable spreadsheet software (e.g., Excel 4.0), 2 monitors (one for operator-computer interface and one for showing a live video image of the microscope view, i.e., a framegrabber, having a resolution of 640 pixels wide and 480 pixels high).
4. Sony 3-C-CD Camera (or the equivalent thereof). The back of the control box has the following settings: Gamma—off; Linear Matrix—off; computer cables are connected to RGB1 and Composite Sync, not RGB2. The front of the control box has the following settings: Color Temp.—3200K; Shutter off; Gain 0; White/Black balance—auto; iris auto; Mode—camera; Detail—12 o'clock position; Phase—0 degrees not 180 degrees; SC-3 o'clock position; H-12 o'clock position. Balance the white light using the light source by pressing the button that says white. Balance the black, after pulling rod with black ball on microscope that deflects the light from raveling to the camera, by pressing the button that says black. Allow the light to warm up and stabilize for 15 minutes before setting the white balance or using the program. The settings for this camera are suitable for equivalent cameras which are also commercially available.

(C) Sample Preparation

Films of the product to be tested are prepared by uniformly depositing the test product onto clear acetate sheets 19×17 cm in size in the desired manner of application, e.g., electrostatic spraying or passing through a mesh as described herein or other desired method of application. The product is allowed to dry under ambient conditions (21 C, 1 atm) for at least 15 minutes prior to image analysis.

Electrostatically sprayable compositions such as described herein may be applied by spraying such that the spray is emitted from the spray device at a distance of 7+/−0.5 inches from the sheet and perpendicular to the sheet. The product is applied by making 10 complete passes over the length of the sheet at a rate of 1 foot/second and at a product flow rate of 9 ml/hour.

(D) Calibration

The camera brightness/contrast is calibrated upon starting the application, and is re-calibrated whenever the microscope lens or lighting is changed. Spatial calibration is also calibrated, however there is a default calibration that is valid when the microscope lens is 1.0× (S1, 0×) and the magnification is 5.0 (default calibration is 1 pixel=2.681 microns). If any other lens or magnification is used, spatial calibration must be conducted.

To perform brightness/contrast calibration, a black and white opacity card (e.g., from Leneta) is used as a standard and is placed under the microscope and positioned so that half the image in the camera monitor is white and the other half is black. The view is focused and the imaging software is run to automatically adjust the camera brightness and contrast. The standard should not be moved during adjustment. If necessary this step is repeated until successful calibration is indicated.

To perform spatial calibration, a spatial calibration standard (a cm ruler or a millimeter graticule slide) is placed under the microscope and brought into focus. Calibration then involves constructing a line in the image, using the cursor, connecting the ends of the standard (about 1 mm long). The length of this line is automatically computed in microns and saved (this calibration may be saved as a default each time the application is used).

(E) Analysis

The analysis is performed after calibration is completed. To perform the analysis, place the acetate sheet coated with the film to be tested on a dark background (e.g., a piece of black glass) under the microscope and focus. A live image acquisition mode is used such that the monitor displays live images. 10 random images are captured and analyzed in accordance with (A) above and the following.

(i) Particle Size Analysis

The threshold value is set to (140:255). The computer will determine the diameter of all of the pixels that it has designated as a particle in accordance with (A)(6) above. The computer calculates the average equivalent diameter of all the relevant particles: A relative diameter is created by taking the number of pixels that are in a given particle and extrapolating a circle and calculating the diameter of the circle. The average diameter is the average of all the diameters, which is the average particle size according to this method. The computer also calculates the standard deviation equivalent diameter of all the relevant particles (the standard deviation of all the equivalent diameters calculated above), which is the standard deviation for the average particle size according to this method.

(ii) Particle Spacing Analysis

Spacing is calculated based on the distance of each foreground pixel of the input binary image with the distance to its nearest background pixel. The analysis involves the following steps:
1. Threshold the image to (127.5:255).
2. Invert the image.
3. Change the inverted image into a binary image.
4. For each foreground pixel in the binary image, calculate the digital distance to the nearest background pixel.
5. Create a 16 bit distance image for the values collected.
6. From the data create a histogram of the distance versus how many pixels are at that distance.
7. Calculate the mean of the histogram (the standard deviation may also be calculated). In this method, the mean is a half distance of the actual spacing between particles and is the relative spacing number reported as the average spacing between particles.

(iii) Coverage Analysis

The coverage analysis involves determining the pixel area of product film having a minimum gray value relative to the total pixel area in a given image. The analysis involves the following steps:
1. Convert the image into 8 bit gray.
2. Threshold the image to (140:255) in the gray scale.
3. Isolate all areas that have a threshold of 140 or above and outline these areas to form connected components (the outlined areas correspond to the product film and are also called foreground).
4. Calculate the numbers of pixels in the area labeled as product (designated as foreground area).
5. Calculate the total number of pixels in the image's total field of view (i.e., all of the pixels in the background and the foreground combined). This is designated the Total Area.
6. Use the following equation to calculate the percent area covered: (Foreground area/Total area)×100=Percent area covered. The percent area covered is the coverage value.

II. COMPOSITIONS (A) Carrier Component

The topical compositions from which the films are formed comprise one or more particulate materials dispersed in a carrier which comprises one or more liquid diluents. Suitable liquid diluents may be volatile or nonvolatile, and polar or non-polar, and include the insulating and conductive materials described below. A variety of such carriers are known in the art of topical compositions, and are generally known to comprise one or more compatible diluents, extenders and the like.

The type of carrier utilized in the present invention depends on the type of product desired. The topical compositions useful in the subject invention may be in a wide variety of product types including liquid or semi-liquid forms. These include, but are not limited to, lotions, creams, gels, sprays, ointments, pastes, and mousses. Compositions useful in the invention may for example comprise a solution of materials having the particulate material dispersed therein, or may comprise an emulsion having the particulate material dispersed therein. The selection of carrier components and amounts depends on the desired product type and is within the level of ordinary skill.

The compositions will typically comprise from about 0.1% to about 35% particulate and from about 5% to about 90% fluid carrier. The compositions generally comprise from about 5% to about 90% liquid diluent. The compositions will preferably have a viscosity of from about 10 to about 50,000 mPas at 10 $\sec^{-1}$ (at 25 degree C., using 60 mm parallel plate with 0.5 mm gap at rate of 10 $\sec^{-1}$).

The composition is preferably electrostatically sprayable, comprising at least one conductive material which is preferably a liquid, more preferably a volatile liquid. The electrostatically sprayable compositions may also comprise one or more insulating materials, at least one of which is preferably liquid and more preferably a volatile liquid. More preferably, the electrostatically sprayable composition comprises an emulsion wherein the insulating material and conductive material are in different phases, even more preferably wherein the insulating material is in the continuous, external phase and the conductive material is in the discontinuous, internal phase. Preferred electrostatically sprayable, topical compositions comprise:
a) from about 2% to about 90% of a conductive material;
b) from about 0% to about 90% of an insulating material; and
c) from about 0.1% to about 35% of a particulate material which is insoluble and immiscible in the composition.

In general, electrostatic spray techniques involve raising the composition to be sprayed to a high electric potential in a spray nozzle to cause the composition to atomize as a spray of electrically charged droplets. The electrically charged droplets seek the closest earthed object to discharge their electric charge, which can be arranged to be the desired spray target.

In order to be electrostatically sprayable, a composition must have a resistivity which enables atomization as a spray of the charged droplets. In preferred compositions, the components of the composition are selected or adjusted such that the composition has a resistivity of from about 0.01 to about 5000 Mega-ohm-cm, more preferably from about 0.01 to about 2000 Mega-ohm-cm, most preferably from about 0.1 to about 500 Mega-ohm-cm. Resistivity is measured using standard, conventional apparatus and methods, generally at 25 degree C. Resistivity can be adjusted as necessary by varying the relative levels of insulating materials and conductive materials. In general, resistivity decreases with increasing percentage of conductive materials and decreasing percentage of insulating materials.

The compositions intended for electrostatic spraying must also have a viscosity which permits electrostatically spraying. Materials of a wide range of viscosities may be suitable for use in the present invention, however the viscosity is preferably sufficiently high to minimize wicking of the composition droplets as they are applied. The tendency to wick depends on the surface tension of the composition and tends to increase with decreasing surface tension of the liquid diluent system. In compositions based on liquid diluents having a relatively low surface tension (i.e., which have a tendency to wet the substrate), it is generally desirable to utilize a viscosity increasing agent to minimize wicking such as the structuring agents or thickeners described herein. Preferably the viscosity is in the range of from about 0.1 to about 50,000 mPas, more preferably from about 0.5 to about 20,000 mPas, most preferably from about 5 to about 10,000 mPas (at 25 degree C, using 60 mm parallel plate with 0.5 mm gap at rate of 10 $\sec^{-1}$).

Conductive Component

Electrostatically sprayable compositions suitable for use herein contain one or more conductive components, more preferably volatile (i.e., having a measurable vapor pressure at 1 atm) and liquid. The conductive material ensures that the composition as a whole can, when in the presence of a non-uniform electric field, generate dielectrophoretic forces great enough to pull the composition toward the region of highest field intensity (hence creating an electrostatic spray). The conductive material preferably has a resistivity of less than 5000 Mega-ohm-cm, more preferably less than about 2000 Mega-ohm-cm, most preferably less than about 500 Mega-ohm-cm. This material preferably also has a relaxation time which is sufficiently long to enable a spray wherein all of the particles have a size of less than 300 microns according to standard light microscopy methods. The conductive material preferably has a relaxation time of from about 1E-7 to 1 seconds, more preferably from about 1E-6 to 1E-2 seconds, most preferably from about 1E-5 to 1E-3 seconds.

Suitable liquid conductive materials include polar solvents, polar aprotic solvents, glycols, polyols, and mixtures thereof. Preferred liquid conductive materials are selected from the group consisting of water, alcohols, glycols, polyols, ketones and mixtures thereof, more preferably alcohols, glycols, polyols (typically comprising about 16 or less carbon atoms) and mixtures thereof. More preferred conductive materials are propylene glycol, butylene glycol, dipropylene glycol, phenyl ethyl alcohol, ethanol, isopropyl alcohol, glycerin, 1,3-butanediol, 1,2-propane diol, isoprene glycol, water, acetone, or a mixture thereof. Particularly preferred conductive materials are propylene glycol, butylene glycol, ethanol, glycerin, water, or a mixture thereof The conductive material is more preferably selected from propylene glycol, ethanol, and mixtures thereof, and is most preferably propylene glycol.

The electrostatically sprayable compositions hereof are more preferably non-aqueous or contain only a small amount of water, e.g. less than about 10% by weight, preferably less than about 5% by weight, even more preferably less than about 1% by weight water. This is because, due to its short relaxation time (about 7E-6 seconds) and low resistivity, compositions containing large amounts of water generally create sprays which are difficult to control in terms of particle size and spacing when electrostatic means are used.

The present compositions may further include non-liquid or non-volatile conductive materials. The total level of conductive materials in electrostatically sprayable compositions is typically from about 2% about 90%. Other conductive materials include solid particles such as metal powders, particles coated with metal or other conductive material, charged species (e.g., salts such as NaCl, or salts used conventionally in buffers in personal care products), and hydrophilic coated polymeric particles.

Insulating Component

Electrostatically sprayable compositions suitable for use herein may also contain one or more insulating components, more preferably volatile and liquid. By "nsulating" it is meant that a material would not itself be suitable for electrostatic spraying (that is, it would not be able to cause sufficient alignment of the dipole molecules in the field to result in the subsequent, necessary net force), typically having a resistivity of greater than about 2000 Mega-ohm-cm, more preferably greater than about 5000 Mega-ohm-cm. For electrostatically sprayable compositions, the total level of insulating materials is typically from about 0% to about 90%.

Preferred insulating materials have a viscosity of about 10,000 mPas or less. Suitable insulating materials are selected from non-polar substances, e.g., oils and other hydrophobic materials. Preferred insulating materials are selected from the group consisting of volatile silicones, volatile hydrocarbons, and mixtures thereof.

Suitable volatile silicones include cyclic polyalkylsiloxanes represented by the chemical formula $[SiR_2—O]_n$ wherein R is an alkyl group (preferably R is methyl or ethyl, more preferably methyl) and n is an integer from about 3 to about 8, more preferably n is an integer from about 3 to about 7, and most preferably n is an integer from about 4 to about 6. When R is methyl, these materials are typically referred to as cyclomethicones. Commercially available cyclomethicones include Dow Corning® 244 fluid having a viscosity of 2.5 centistokes, and a boiling point of 172° C., which primarily contains the cyclomethicone tetramer (i.e. n=4), Dow Corning® 344 fluid having a viscosity of 2.5 centistokes and a boiling point of 178° C., which primarily contains the cyclomethicone pentamer (i.e. n=5), Dow Corning® 245 fluid having a viscosity of 4.2 centistokes and a boiling point of 205° C., which primarily contains a mixture of the cyclomethicone tetramer and pentamer (i.e. n=4 and 5), and Dow Corning® 345 fluid having a viscosity of 4.5 centistokes and a boiling point of 217°, which primarily contains a mixture of the cyclomethicone tetramer, pentamer, and hexamer (i.e. n=4, 5, and 6). Dow Coming® 244 fluid and Dow Coming® 344 fluid are preferred cyclomethicones.

Other suitable volatile silicones are linear polydimethyl siloxanes having from about 3 to about 9 silicon atoms and the general formula $(CH_3)_3Si—O—[—Si(CH_3)_2—O—]_n—Si(CH_3)_3$ where n=0–7. These silicones are available from various sources including Dow Coming Corporation and General Electric.

Suitable volatile hydrocarbons include those having boiling points in the range of 60–260° C., more preferably hydrocarbons having from about $C_8$ to about $C_{20}$ chain lengths, most preferably $C_8$ to $C_{20}$ isoparaffins. Preferred isoparaffins are isododecane, isohexadecane, isoeocosane, 2,2,4-trimethylpentane, 2,3-dimethylhexane and mixtures thereof. Most preferred is isododecane, for example available as Permethyl 99A from Permethyl Corporation.

Suitable non-volatile insulating materials include non-volatile oils, such as disclosed in U.S. Pat. Nos. 5,800,816 and 5,505,937.

For electrostatically sprayable compositions, the relative total levels of the insulating and conductive materials may vary, provided that sufficient conductive material is present such that the composition realizes the electrical potential during spraying. The compositions preferably comprise a total of from about 0% to about 90% more preferably from about 10% to about 70%, most preferably from about 20% to about 60%, of insulating material and from about 2% to about 90%, more preferably from about 5% to about 70%, most preferably from about 10% to about 60% of conductive material. In general, sprayability improves with the level of conductive material such that it will normally be advantageous to maximize the level of conductive materials. Preferred compositions comprise a weight ratio of insulating material to conductive material (disregarding any non-conductive particulate materials) of from about 10:1 to about 1:12. For the preferred electrostatically sprayable emulsion having an insulating external phase and conductive internal phase, the preferred weight ratio of insulating material to conductive material (disregarding any non-conductive particulate materials) is from about 0.2:1 to about 8:1, more preferably about 1:1.

(B) Powder Component

The compositions of the invention also comprise one or more powder materials, which are generally defined as dry, particulate matter having a particle size of from 0.001 to 150 microns, preferably 0.01 to 100 microns. The powder materials may be colored or non-colored (e.g., white or essentially clear), and may provide one or more benefits to the composition or skin such as coloration, light diffraction, oil absorption, translucency, opacification, pearlescence, matte appearance, lubricious feel, skin coverage and the like. These materials are well known in the art and are commercially available. Selection of the particular type and level of a given powder material for a particular purpose in a given product is within the skill of the artisan. Preferred ranges of non-conductive particulate matter are about 0.1% to 35% of the total composition.

Suitable powders include various organic and inorganic pigments which color the composition or skin. Organic pigments are generally various types including azo, indigoid, triphenylmethane, anthraquinone, and xanthine dyes which are designated as D&C and FD&C blues, browns, greens, oranges, reds, yellows, etc. Inorganic pigments are generally insoluble metallic salts of certified color additives, referred to as lakes or iron oxides. Suitable pigments include those generally recognized as safe, and listed in C.T.F.A. *Cosmetic Ingredient Handbook*, First Edition, Washington D.C. (1988). Specific examples are red iron oxide, yellow iron oxide, black iron oxide, brown iron oxide, ultramarine, FD&C Red, Nos. 2, 5, 6, 7, 10, 11, 12, 13, 30 and 34; FD&C Yellow No 5, Red 3, 21, 27, 28, and 33 Aluminum Lakes, Yellow 5, 6, and 10 Aluminum Lakes, Orange 5 Aluminum Lake, Blue 1 Aluminum Lake, Red 6 Barium Lake, Red 7 Calcium Lake, and the like.

Other useful powder materials include talc, mica, titanated mica (mica coated with titanium dioxide), iron oxide titanated mica, magnesium carbonate, calcium carbonate, magnesium silicate, silica (including spherical silica, hydrated silica and silica beads), titanium dioxide, zinc oxide, nylon powder, polyethylene powder, ethylene acrylates copolymer powder, methacrylate powder, polystyrene powder, silk powder, crystalline cellulose, starch, bismuth oxychloride, guanine, kaolin, chalk, diatomaceous earth, microsponges, boron nitride and the like. Additional powders useful herein are described in U.S. Pat. No. 5,505,937 issued to Castrogiovanni et al. Apr. 9, 1996.

Of the components useful as a matte finishing agents, low luster pigment, talc, polyethylene, hydrated silica, kaolin, titanium dioxide, titanated mica and mixtures thereof are preferred.

Micas, boron nitride and ethylene acrylates copolymer (e.g., EA-209 from Kobo) are preferred for imparting optical blurring effects through light diffraction and for improving skin feel, e.g., by providing a lubricious feel. Another particulate material for improving skin feel is SPCAT 12 (a mixture of talc, polyvinylidene copolymer, and isopropyl titanium triisostearate).

Preferred powders for absorbing oil are spherical, non-porous particles, more preferably having a particle size less than 25 microns. Examples of some preferred oil absorbing powders are Coslin C-100 (a spherical oil absorber commercially available from Englehard), Tospearl (spherical silica commercially available Kobo Industries), ethylene acrylates copolymer such as noted above, and SPCAT 12.

The powders may be surface treated with one or more agents, e.g., with lecithin, amino acids, mineral oil, silicone oil, or various other agents, which coat the powder surface, for example, to render the particles hydrophobic or hydrophilic. Such treatment may be preferred to improve ease of formulation and stability.

In a preferred embodiment the composition is in the form of a cosmetic foundation. As used hereinafter, the term "foundation" refers to a liquid or semi-liquid skin cosmetic which includes, but is not limited to lotions, creams, gels, pastes, and the like. Typically the foundation is used over a large area of the skin, such as over the face, to provide a particular look. Foundation compositions of the invention typically comprise from about 2% to about 20% pigment for coloration, and from about 2% to about 15% of additional non-pigmented particulates.

(C) Optional Components

The compositions hereof optionally comprise additional components such as are conventionally used in topical products, e.g., for providing some esthetic or functional benefit to the composition or skin, such as sensory benefits relating to appearance, smell, or feel, therapeutic benefits, or prophylactic benefits (it is to be understood that the above-described required materials may themselves provide such benefits).

The CTFA Cosmetic Ingredient Handbook, Second Edition (1992) describes a wide variety of nonlimiting cosmetic and pharmaceutical ingredients commonly used in the skin care industry, which are suitable for use in the topical compositions of the present invention. Such other materials may be dissolved or dispersed in the composition, depending on the relative solubilities of the components of the composition.

Compositions to be delivered using the present invention are preferably generally liquid in form. Any adjunct materials which are present may be liquid, solid or semi-solid at room temperature, though they should be selected so as to permit deposition of the composition to form the films hereof. For enhancing electrostatic spraying, preferred compositions have a solids content of about 35 weight % or less. In this regard, "solids" refers to particulate materials which are not soluble or miscible in the composition, and includes particulate pigments and oil absorbers.

Examples of suitable topical ingredient classes include: anti-acne agents, anti-inflammatory agents, anti-cellulite agents, anti-microbial agents, anti-fungal actives, antioxidants, radical scavengers, chelating agents, desquamation actives, skin bleaching and lightening agents, skin-conditioning agents (e.g., humectants, including miscellaneous and occlusive), other skin-feel agents, moisturizers, skin repair ingredients including agents for preventing, retarding, and/or reversing skin lines, wrinkles, or atrophy, skin soothing and/or healing agents, self-tanning actives, sunscreens, sunblocks, vitamins and derivatives thereof, abrasives, other oil absorbents, astringents, skin sensates, film formers or materials, e.g., polymers, for aiding the film-forming properties and/or substantivity of the composition, including materials which impart extended wear and/or transfer resistance to the composition, other colorants, pigments and dyes, essential oils, fragrance, thickeners, structuring agents, emulsifiers, solubilizing agents, anti-caking agents, antifoaming agents, binders, buffering agents, bulking agents, denaturants, pH adjusters, propellants, reducing agents, sequestrants, cosmetic biocides, and preservatives.

Preferred compositions of the invention comprise one or more ingredients selected from the group consisting of materials which impart transfer or wear resistant properties, structuring agents or thickeners, emulsifiers, co-solubilizers and mixtures thereof. Nonlimiting examples of these components include the following:

Materials for enhancing wear or transfer resistance. One or more materials for imparting wear and/or transfer resistant properties, e.g., via film forming or substantive properties, may be used in the present compositions. Such materials are typically used in an amount of from about 0.5% to about 20%.

Such materials include film forming polymeric materials. While the level of film forming polymeric material may vary, typically the film forming polymeric material is present in levels of from about 0.5% to about 20% (e.g., from about 1 to about 15%), preferably from about 0.5% to about 10% by weight, more preferably from about 1% to about 8% by weight. Preferred polymers form a non-tacky film which is removable with water used with cleansers such as soap.

Examples of suitable film forming polymeric materials include:

a) sulfopolyester resins, such as AQ sulfopolyester resins, such as AQ29D, AQ35S, AQ38D, AQ38S, AQ48S, and AQ55S (available from Eastman Chemicals);
b) polyvinylacetate/polyvinyl alcohol polymers, such as Vinex resins available from Air Products, including Vinex 2034, Vinex 2144, and Vinex 2019;
c) acrylic resins, including water dispersible acrylic resins available from National Starch under the trade name "Dermacryl", including Dermacryl LT;
d) polyvinylpyrrolidones (PVP), including Luviskol K17, K30 and K90 (available from BASF), water soluble copolymers of PVP, including PVP/VA S-630 and W-735 and PVP/dimethylaminoethylmethacrylate Copolymers such as Copolymer 845 and Copolymer 937 available from ISP, as well as other PVP polymers disclosed by E. S. Barabas in the *Encyclopedia of Polymer Science and Engineering*, 2 Ed. Vol. 17 pp. 198–257;
e) high molecular weight silicones such as dimethicone and organic-substituted dimethicones, especially those with viscosities of greater than about 50,000 mPas;
f) high molecular weight hydrocarbon polymers with viscosities of greater than about 50,000 mPas;
g) organosiloxanes, including organosiloxane resins, fluid diorganopolysiloxane polymers and silicone ester waxes.

Examples of these polymers and cosmetic compositions containing them are found in PCT publication Nos. WO96/33689, published Oct. 31, 1996; WO97/17058, published May 15, 1997; and U.S. Pat. No. 5,505,937 issued to Castrogiovanni et al. Apr. 9, 1996, all incorporated herein by reference. Additional film forming polymers suitable for use herein include the water-insoluble polymer materials in aqueous emulsion and water soluble film forming polymers described in PCT publication No. WO98/18431, published May 7, 1998. Examples of high molecular weight hydrocarbon polymers with viscosities of greater than about 50,000 mPas include polybutene, polybutene terephthalate, polydecene, polycyclopentadiene, and similar linear and branched high molecular weight hydrocarbons.

Preferred film forming polymers include organosiloxane resins comprising combinations of $R_3SiO_{1/2}$ "M" units, $R_2SiO$ "D" units, $RSiO_{3/2}$ "T" units, $SiO_2$ "Q" units in ratios to each other that satisfy the relationship $R_nSiO_{(4-n)/2}$ where n is a value between 1.0 and 1.50 and R is a methyl group. Note that a small amount, up to 5%, of silanol or alkoxy functionality may also be present in the resin structure as a result of processing. The organosiloxane resins must be solid at about 25° C. and have a molecular weight range of from about 1,000 to about 10,000 grams/mole. The resin is soluble in organic solvents such as toluene, xylene, isoparaffins, and cyclosiloxanes or the volatile carrier, indicating that the resin is not sufficiently crosslinked such that the resin is insoluble in the volatile carrier. Particularly preferred are resins comprising repeating monofunctional or $R_3SiO_{1/2}$ "M" units and the quadrafunctional or $SiO_2$ "Q" units, otherwise known as "MQ" resins as disclosed in U.S. Pat. No. 5,330,747, Krzysik, issued Jul. 19, 1994, incorporated herein by reference. In the present invention the ratio of the "M" to "Q" functional units is preferably about 0.7 and the value of n is 1.2. Organosiloxane resins such as these are commercially available such as Wacker 803 and 804 available from Wacker Silicones Corporation of Adrian, Mich., and G. E. 1170-002 from the General Electric Company.

Other materials for enhancing wear or transfer resistance include trimethylated silica. Suitable silicas of this type and cosmetic compositions containing them are described in U.S. Pat. No. 5,800,816 issued to Brieva et al., incorporated herein by reference.

Structuring or thickening agents. Compositions hereof may also comprise one or more structuring or thickening agents., e.g., to enhance the stability of the composition, preferably upon exposure to an electric field applied during an electrostatic spray process. The compositions typically comprise a total of from about 0.5% to about 20% of such agents.

Suitable structuring or thickening agents can be selected from the group consisting of silicones, waxes, clays, silicas, salts, natural and synthetic esters, fatty alcohols, and mixtures thereof. Nonlimiting examples of these structuring or thickening agents are described below.

Suitable silicones include alkyl siloxane gellants, high molecular weight dimethicones (fluids greater than 1000 mPas), and high molecular weight alkyl, hydroxyl, carboxyl, amino, and/or fluoro- substituted dimethicones (fluids greater than 1000 mpas). Preferred silicone gellants are described in U.S. Pat. No. 5,654,362 and 5,880,210, and include cyclomethicone and dimethicone crosspolymers (e.g., Dow Corning 9040).

Waxes can be defined as lower-melting organic mixtures or compounds of high molecular weight, solid at room temperature and generally similar in composition to fats and oils except that they contain no glycerides. Some are hydrocarbons, others are esters of fatty acids and alcohols. Suitable waxes may be selected from the group consisting of natural waxes including animal waxes, vegetable waxes, and mineral waxes, and synthetic waxes including petroleum waxes, ethylenic polymers, hydrocarbon waxes (e.g., Fischer-Tropsch waxes), ester waxes, silicone waxes, and mixtures thereof. Synthetic waxes include those disclosed in Warth, *Chemistry and Technology of Waxes*, Part 2, Reinhold Publishing (1956).

Specific examples of waxes include beeswax, lanolin wax, shellac wax, carnauba, candelilla, bayberry, jojoba esters, behenic acid waxes (e.g., glyceryl behenate which is available from Gattifosse as Compritol®, ozokerite, ceresin, paraffin, microcrystalline waxes, polyethylene homopolymers, polymers comprising ethylene oxide or ethylene (e.g., long chained polymers of ethylene oxide combined with a dihydric alcohol, namely polyoxyethylene glycol, such as Carbowax available from Carbide and Carbon Chemicals company; long-chained polymers of ethylene with OH or another stop length grouping at end of chain, including Fischer-Tropsch waxes as disclosed in Warth, supra, at pages 465–469 and specifically including Rosswax available from Ross Company and PT-0602 available from Astor Wax Company), $C_{24-45}$ alkyl methicones, $C_8$ to $C_{50}$ hydrocarbon waxes, alkylated polyvinyl pyrrolidones (e.g., "Ganex" alkylated polyvinylpyrrolidines available from the ISP Company), fatty alcohols from C20 to C60 (e.g., "Unilins", available from Petrolite Corporation), and mixtures thereof.

Water dispersible and oil dispersible clays may be useful to provide structure or thickening. Suitable clays can be selected, e.g., from montmorillonites, bentonites, hectorites, attapulgites, sepiolites, laponites, silicates and mixtures thereof.

Suitable water dispersible clays include bentonite and hectorite (such as Bentone EW, LT from Rheox); magnesium aluminum silicate (such as Veegum from Vanderbilt Co.); attapulgite (such as Attasorb or Pharamasorb from Engelhard, Inc.); laponite and montmorillonite (such as Gelwhite from ECC America); and mixtures thereof.

Suitable oil dispersible clays include organophilically modified bentonites, hectorites and attapulgites. Specific commercially available examples of these clays include Bentone 34 (Rheox Corp.)—Quaternium-18 Bentonite; Tixogel VP (United Catalysts)—Quaternium-18 Bentonite; Bentone 38 (Rheox Corp.)—Quaternium-18 Hectorite; Bentone SD-3 (Rheox Corp.)—Dihydrogenated Tallow Benzylmonium Hectorite; Bentone 27 (Rheox Corp.)—Stearalkonium Hectorite; Tixogel LG (United Catalysts)—Stearalkonium Bentonite; Claytone 34 (Southern Clay) Quatemium-18 Bentonite; Claytone 40 (Southern Clay) Quaternium-18 Bentonite; Claytone AF (Southern Clay) Stearalkonium Bentonite; Claytone APA (Southern Clay) Stearalkonium Bentonite; Claytone GR (Southern Clay) Quaternium- 18/Benzalkonium Bentonite; Claytone HT (Southern Clay) Quaternium-18/Benzalkonium Bentonite; Claytone PS (Southern Clay) Quaternium-18/Benzalkonium Bentonite; Claytone XL (Southern Clay) Quaternium-18 Bentonite; and Vistrol 1265 (Cimbar)—Organophilic Attapulgite. These organophilic clays can be purchased as predispersed organophilic clay in either an oil or an organic solvent. The materials are in the form of a heavy paste that can be readily dispersed into the formulation. Such materials include Mastergels by Rheox, United Catalysts, and Southern Clay.

Other structuring or thickening agents include fumed silicas and alkali metal or ammonium halides. Examples of fumed silicas include Aerosil 200, Aerosil 300, and the alkyl-substituted fumed silicas such as Aerosil R-100, 200, 800, and 900 series of materials, all available from the DeGussa Corporation.

Preferred structuring agents are those which are substantially inert to the distribution of charge through a fluid, e.g., waxes and high molecular weight silicones and hydrocarbons.

Emulsfiers. The compositions hereof may contain one or more emulsifiers, e.g., to enhance the formation and stability of the composition. Compositions of the invention typically comprise from about 0.5% to about 10%, preferably from about 1% to about 5%, more preferably from about 1.5% to about 3% of one or more emulsifiers.

The hydrophilic-lipophilic balance value of the emulsifier (herein referred to as HLB) is chosen so as to optimally lower the interfacial tension between two phases of significantly different surface tension. For a polar-in-non-polar system, HLB ranges are typically from about 4 to about 8. For a non-polar-in-polar system, HLB ranges are typically from about 12 to about 20. HLB factors are described in Wilkinson and Moore, *Harry's Cosmeticology*, 7th Ed. 1982, p. 738 and Schick and Fowkes, Surfactant Science Series, Vol. 2. *Solvent Properties of Surfactant Solutions*, p 607. Exemplary emulsifiers include those disclosed in the C.T.F.A. Cosmetic Ingredient Handbook, 3rd Ed., Cosmetic and Fragrance Assn., Inc., Washington D.C. (1982) pp. 587–592; and Remington's Pharmaceutical Sciences, 15th Ed. 1975, pp. 335–337; and McCutcheon's Volume 1, *Emulsifiers & Detergents*, 1994, North American Edition, pp. 236–239.

Particularly useful emulsifiers for the present compositions include polydiorganosiloxane-polyoxyalkylene copolymers. Such polymers are described in U.S. Pat. No. 4,268,499, incorporated herein by reference. Suitable copolymers of this type are known and many are available commercially. A preferred emulsifier of this type is known by its CTFA designation as dimethicone copolyol. Preferred emulsifiers are further disclosed in U.S. Pat. No. 5,143,722, incorporated herein by reference.

Another preferred class of emulsifiers are high molecular weight polymeric emulsifiers such as are effective for stabilizing glycol/polyol-in-hydrocarbon systems (e.g., Arlacel P135 commercially available from Unichema).

Co-solubilizers. The compositions hereof may contain one or more co-solubilizers, e.g., to enhance the formation and stability of the composition. The co-solubilizer is especially useful to bridge compatibility of two materials which are normally incompatible, resulting in the creation of a single, stable phase. Co-solubilizers may therefore be particularly preferred in the single phase electrostatically sprayable compositions described herein. When used, compositions of the invention typically comprise from about 0.5% to about 10%, preferably from about 1% to about 5%, more preferably from about 1.5% to about 3% co-solubilizer.

Suitable co-solubilizers are best chosen using a solubility parameter scale as is described in "Solubility: Effects in Product, Package, Penetration, and Preservation," by C. D. Vaughan, *Cosmetics and Toiletries*, Vol. 103, Ocober 1988. Based on the solubility parameter of two incompatible materials, a third material with a solubility parameter in between that of the two incompatible materials may sometimes be found which is independently compatible with the two incompatible materials. When all three materials are then combined, they may exhibit the properties of a single stable phase, as could be measured, visually for example, via a light microscope.

Co-solubilizers can be polar fluids, non-polar fluids, polar aprotic solvents, or amphiphilic materials and are chosen from these broad categories to fit the needs of the two incompatible materials to create a single phase.

Particularly useful co-solubilizers include the polydiorganosiloxane-polyoxyalkylene copolymers described, including the polymers described in U.S. Pat. No. 4,268,499, as well as the surfactants disclosed in U.S. Pat. No. 5,143,722. Dimethicone copolyol is preferred.

(D) Particular Embodiments of Electrostatically Sprayable Topical Compositions

Electrostatically sprayable compositions useful in the invention may comprise a solution of insulating and conductive materials having the particulate material dispersed therein (hereinafter also referred to as "single phase", reflecting the solution), or may comprise an emulsion comprising an insulating phase and a conductive phase having the particulate material dispersed therein (hereinafter also referred to as "multiple phase", reflecting the emulsion).

Preferred electrostatically sprayable compositions comprise an emulsion wherein the insulating material and conductive material are in different phases. The insulating or conductive materials may be in either the continuous external phase or the discontinuous internal phase. Preferably, the insulating material is in the continuous, external phase and the conductive material is in the discontinuous, internal phase.

Preferred electrostatically sprayable, single phase compositions comprise:

(a) from about 2% to about 90% of a conductive material;

(b) from about 0.1% to about 35% of a particulate material which is insoluble and immiscible in the composition;

(c) from about 0.5% to about 25% of a structuring agent or thickener for stabilizing the composition; and optionally one or more of (d) from about 0% to about 80% of a liquid insulating material;

(e) from about 0% to about 15% of a co-solubilizer; and (f) from about 0.1% to about 20% of a material for imparting wear or transfer resistance.

Preferred electrostatically sprayable, multiple phase compositions comprise:

(a) from about 5% to about 70% of a liquid insulating material;

(b) from about 5% to about 65% of a conductive material;

(c) from about 0.5% to about 30% of a particulate material which is insoluble and immiscible in the composition; and optionally one or more of:

(d) from about 0% to about 20% of a structuring agent or thickener for stabilizing the composition;

(e) from about 0.1% to about 20% of an emulsifier; and (f) from about 0.1% to about 20% of a material for imparting wear or transfer resistance.

Suitable electrostatically sprayable topical compositions are also described in copending, commonly assigned U.S. Patent Applications: Attorney's Docket Case 7730P, U.S. Ser. No. 60/149566, entitled "Electrostatically Sprayable Topical Compositions Having Insulating External Phase and Conductive Internal Phase", Attorney's Docket Case 7731P, U.S. Ser. No. 60/149565, entitled "Stable, Electrostatically Sprayable Topical Compositions", and Attorney's Docket Case 7732P, U.S. Ser. No 60/149585, entitled "Wear Resistant Topical Compositions Having Improved Feel", all filed on Aug. 18, 1999 in the name of Thomas E. Rabe et al., and all incorporated herein by reference.

III) METHOD OF MAKING/USING THE INVENTION (A) Electrostatic Spray Techniques

The films of the present invention are preferably formed by electrostatically spraying a topical composition capable of such application such as described herein. In general, this method involves raising the composition to be sprayed to a high electric potential in a spray nozzle to cause the composition to atomize as a spray of electrically charged droplets. The electrically charged droplets seek the closest earthed object to discharge their electric charge, which can be arranged to be the desired spray target.

For use in the present invention, the hardware and electrical componentry and circuitry may be of any suitable construction and design. The art of electrostatic spraying contains many examples of suitable apparatus which may be used in the present invention and such disclosures of such apparatus or particular features thereof may be applied either singly or in combination to the spray systems of the present invention. Examples of suitable electrostatic spraying hardware include those described in the following publications: U.S. Pat. Nos. 4,549,243; 4,561,037; 4,663,639; 4,854,506; 4,846,407; 5,121,884; 5,222,663; 5,222,664; 5,221,050; 5,290,600; 5,337,963; 5,292,067; 5,490,633; 5,184,778; 5,503,335; 5,684,666; and 4,776,515; Japanese patent No. 1,932,551; JP-A-56-97214; Canadian Patent Application No. 2018551-1; GB-A-1393333; GB-A-15697007, GB-A-2092025; GB-A-2061769; GB-A-2073052; Taiwanese Patent No. NI-64734; EPO Application No. 94924355.4 (Publication No. 716626); EPO Application No 95915955.9 (Publication No. 748256); EPO Application No. 95916790.9 (Publication No. 748257); EPO Application No. 94931643.4 (Publication No 789626); EPO Application No. 95932065.6 (Publication No. 776253); EPO Application No. 95932063.1 (Publication No. 785823); EP-A-029301; EP-A-253539; EP-A-224352; EP-A-031649; EP-A-132062; EP-A-163390; EP-A-171184; EP-A-234842; EP-A-243031; EP-A-368494; EP-A-441501; EP-A-468735, EP-A-468736; PCT Application No. GB96/01286 (Publication No. 096/40441); PCT Application No. GB97/00376 (Publication No. 097/31718); PCT Application No. GB97/02746; and WO-A-85/00761. Preferred electrostatic spray devices are disclosed in copending, commonly assigned U.S. patent applications Attorney's Docket No. 7711, entitled "Hand-Held Electrostatic Sprayer Apparatus" filed in the names of Chinto B. Gaw et al. on Aug. 18, 1999; and Attorney's Docket No. 7712, entitled "Disposable Cartridge for Use in a Hand-Held Electrostatic Sprayer Apparatus" filed in the name of Chinto B. Gaw et al. on Aug. 18, 1999, both incorporated herein by reference.

Preferred devices include an apparatus suitable for small-scale personal use which has a reservoir for containing the topical composition, at least one delivery means, e.g., a nozzle, in communication with the reservoir; a high voltage generator generating voltage in the range of 1 to 26 kilovolts (e.g., from 12 to 26 kilovolts) powered from a portable or non-portable (preferably portable) electricity source; and control means for selectively applying the high voltage from the generator to the at least one delivery means. In use, the control means is actuated to electrostatically spray the topical composition from the at least one delivery means directly onto the skin at an intended site.

As will be appreciated by persons skilled in the art, particular constructional features and design and electrical and other operating parameters of such apparatuses may be selected or adjusted as necessary, in the context of the present invention, in accordance with the desired functioning characteristics, as for example dictated by the composition to be sprayed and/or the needs or wishes of a user. Features of the apparatus of the present invention which may be so selected and/or adjusted include for example: voltage generated by the high voltage generator and power source, electric field strength in or in the region of the product delivery means, flow rate of the product to be sprayed from the reservoir to and out of the delivery means, size and configuration of the delivery means itself and construction and properties of any product feed mechanism utilized between the reservoir and the output of the delivery means.

The size and configuration of the one or more delivery means in the apparatus of the invention may be of any suitable form and again may be selected in association with other parameters to give an optimized functioning electrostatic spray delivery system. Commonly the or each delivery means will be in the form of a nozzle, preferably of insulating or semi-insulating material such as plastics or various polymers, as is well known in the art. In one preferred form of nozzle, a conduit for carrying the product to be sprayed terminates in an orifice at the tip of the nozzle, from which orifice the product is ejected for example initially as a ligament but in any event eventually dispersing as a spray of charged droplets. The orifice preferably has a diameter of not greater than about 800 microns (e.g., from 508–762 microns or 0.020"–0.030"). Even more preferably the orifice has a diameter of from about 500 to about 750 microns.

The delivery means may advantageously include metering means to provide a dosing mechanism for delivering a predetermined fixed amount of material from the or each nozzle. Such an expedient may for example be useful in conjunction with a system having a controlled flow rate. In preferred embodiments of the apparatus of the invention, the or each delivery means is in communication, i.e. preferably fluid communication, with the reservoir or reservoirs (if for example more than one material or composition is to be desired to be sprayed from the same apparatus or even the same delivery means) by virtue of product feed means. In one preferred form, such feed means may comprise an insulator having a channel between the nozzle and the product reservoir, through which the product to be sprayed flows before reaching the point of high electric field strength where it is dispersed as a charged spray of droplets or particles. In another preferred form the feed means may comprise a hollow conduit through which the composition passes under the effect of capillary action.

As is well known in the art, the apparatus according to the invention preferably includes a trigger (i.e. a manual control means) or alternatively an automatic control means to selectively apply the high voltage from the generator to the or each delivery means to electrostatically spray the composition onto the skin. Any other suitable control means however, e.g. which automatically control actuation of the system, may be used, as will be appreciated by persons skilled in the art.

In preferred embodiments of the invention, voltages generated by the high voltage generator from the power source are in the range of from about 1 to about 26 kilovolts, more preferably from about 6 to about 20 kilovolts. The most suitable voltage for a given system may depend upon the product to be sprayed, as well as other parameters, all of which will generally be selected to give an overall optimized system. Voltage may be applied at constant positive or alternating polarity, however positive polarity is preferred.

Electric field strengths which are responsible for the spraying action of the electrostatic apparatus will be largely dependent upon the voltage applied. However, field strengths may be controlled or adjusted if necessary, for example by changes in nozzle configuration or geometry and/or the use of field intensifying electrodes, which are well known in the art cited above.

The particle size, particle spacing and coverage values of the present films are influenced by the product spray flow rate, the rate of product application to the skin, and the amount of product applied to the skin. In general, particle size increases with increasing resistivity, decreasing voltage, and increasing flow rate, particle spacing increases with increasing voltage and decreasing deposition amount, and coverage value increases with increasing flow rate and increasing deposition amount.

Optimum flow rates of material to be sprayed will generally depend upon the composition of the product itself, and may be selected appropriately on that basis preferably so as to avoid sensory negatives. Also, as already mentioned with respect to viscosity of the sprayable material, a suitable flow rate may be selected depending upon the particular delivery regime and/or habit or needs of a user. Generally it will be desired to utilize lower flow rates with concentrated materials in order to better control the deposition of the composition. By way of example, preferred flow rates of compositions for delivery in accordance with embodiments of the invention are in the range of from about 0.036 to about 1800 ml/hr (0.00001 to about 0.5 ml/sec), more preferably from about 0.1 to about 360 ml/hr (0.0001 to about 0.1 ml/sec), even more preferably from about 0.1 to 100 ml/hr, most preferably from about 1 to about 30 ml/hr per the delivery means. Particularly preferred applications utilize a higher speed flow rate of from about 4 to about 18 ml/hr (preferably about 9 ml/hr), and a lower speed flow rate of from about 2.4 to about 10.8 ml/hr (preferably about 7.2 ml/hr), where the low speed is about 0.2 to 0.8 times the high speed.

In general, as the flow rate increases it will be desired to utilize a higher voltage in order to provide optimal sprayability and small sprayed particle sizes. In a preferred embodiment, the composition is sprayed at a flow rate of from about 0.1 to about 100 ml/hr, a voltage of from about 1 kV to about 26 kV (preferably about 1 kV to about 20 kV), and an application rate of from about 0.01 mg composition/$cm^2$ of skin to about 12 mg composition/$cm^2$ of skin. Relatively high solids compositions such as foundations are typically applied at a rate of about 1 mg/$cm^2$ skin; relatively low solids compositions such as skin lotions are typically applied at a rate of about 5 to 6 mg/$cm^2$ skin. Relatively low solids compositions such as skin lotions are typically delivered at a flow rate of from about 50 to about 60 ml/hr. Relatively high solids compositions such as foundations are preferably electrostatically sprayed at said application rate, at a flow rate of from about 1 to about 30 ml/hr and a voltage of from about 6 kV to about 20 kV. A voltage range of from about 3 kV to about 20 kV is preferred.

Total product application amounts, in terms of amount of product sprayed per $cm^2$ skin, should be less than about 6 mg/$cm^2$ skin. An exemplary application amount is about 0.8 mg/$cm^2$, which tends to provide about a 30–40% coverage value.

The product is typically applied at a rate of 0.005 sec/$cm^2$ skin area to 6 sec/$cm^2$ skin area, more preferably rate of 0.01 sec/$cm^2$ skin area to 3 sec/$cm^2$ skin area, most preferably rate of 0.05 sec/$cm^2$ skin area to 2 sec/$cm^2$ skin area.

(B) Preferred Usage Instructions for Electrostatic Application

Electrostatically sprayable compositions may be applied by a second party (including robotic means) or the end-user of the composition. The present invention also relates to instructions for using an electrostatic spray device to apply topical compositions to the face, especially foundation compositions, and especially second-party and self-application techniques, context, and methods of training self-application.

a) Application Techniques

It has been found that improved results are achieved by observing certain directions relating to distance of the device (particularly the nozzle) from the target application area (the face), the rate of application of product to the skin (including flow rate and device speed settings), and motion of the device during application (including the direction and character of the motion).

In use, the device is held or otherwise positioned so as to efficiently deliver the spray to the target facial area and to avoid obstruction of the spray.

In general, the device is held or positioned sufficiently distant from the target such that the spray pattern spreads sufficiently and does not tend to form lines or other undesirable concentrated effects on the target substrate, and close enough such that the spray adequately grounds to the target so as to deliver optimum coverage and even-ness of laydown. Typically, the device is held or positioned such that the nozzle is from about 3–4 inches (9–13 cm) from the target facial area.

During self-application, it is best to keep one or both eyes open when applying to areas of the face below the nose, and closed when applying to areas of the face above the nose. When self-applying while the eyes are closed, it can be helpful to appropriately judge the distance with which to hold the device from the face, by first stretching the arm all the way out straight (until the feel of the spray mist on the face can no longer be felt clearly) and then bending the elbow to bring the device closer, slowly, until the spray mist is first clearly felt. This typically leads to ensuring that the device stays about 3–4 inches from the applier's face.

For improved even-ness of coverage, the device should be kept moving during application, preferably at a steady pace with a sweeping motion, without stopping in place while the device is operating. In general, the preferred pace is such that in one second one can usually transverse the forehead, or make two passes over a single cheek. depending on the facial size. The swath areas may be partially overlapped, such as occurs with a Zamboni smoothing ice. In a typical 60–90 second application, each facial area is typically passed over 2–8 times.

In a preferred technique, the composition is applied following the contours of the face and in four sections. First, smooth horizontal strokes are made across the forehead. Product is then applied to each side of the face utilizing back and forth sweeping, semi-circular motions following the natural contours of the cheekbone working down to the chin from the side of the face to the center of the face. While applying to the cheeks, it is important to avoid the fourth region, the nose, which is preferably sprayed last since its relative height tends to preferably attract spray. The nose is then sprayed, if needed, along with the area above the upper lip. Where the wearer has visible facial hair, it may be preferred to tilt the nozzle slightly downward to minimize accentuating the visibility of the hair. Also, when first self-applying it is preferred to begin with the jaw line and work "up" the face until one becomes more comfortable with the application process. This allows the wearer to keep her eyes open initially and see where the spray is going on the face, and helps for judging how far away from the face she may be with the device.

Improved results have also been found where the applicant utilizes two or more speeds for applying the product. The preferred use is typically to use a faster speed (higher flow rate) for all-over-face coverage and a slower speed for spot coverage. Preferred is a higher speed flow rate of from about 4 to about 18 ml/hr (preferably about 9 ml/hr), and a lower speed flow rate of from about 2.4 to about 10.8 ml/hr (preferably about 7.2 ml/hr), where the low speed is about 0.2 to 0.8 times the high speed The slow speed allows a more controlled build up of coverage in a specified area without unintentional overapplication. In general, the application process is designed so as to avoid overapplication, resulting in an unnatural look and/or uneven application, but to provide sufficient coverage. It can be helpful for a second party to first view the user with their typical facial makeup in order to identify likely coverage objectives. It is also helpful to utilize a stepwise application, involving at least one sequence of overall application and optionally spot coverage, so that the applicant or user can titrate to the desired appearance.

A typical application process involves the following steps:
1) Apply all over the face using a relatively fast speed/flow rate designed to apply product at a rate of about 9 milliliters/hour;
2) judge whether or not more coverage is needed, and if so where and how much more;
3a) If more product is desired in "spot" areas, e.g., age spots, acne, red areas, dark areas, apply additional spray to the specific areas defined using a slow speed designed to apply about 5–7 milliliters/hour;
3b) If more product is desired "all-over", repeat step (1);
4) Iterate Steps 2 and 3 until the desired coverage is obtained.

The overall time for application tends to be from about 0.5 to 3 minutes (generally from about 60 to about 90 seconds).

b) Context

When instructing someone to apply product either to themselves or others, it has been found that the context with which the first application or demonstration is made is very important to help the end-user feel comfortable and positive about the application experience. The context is preferably designed to provide the user with visible and tactile expectations. It preferably includes the steps of reviewing safety, explaining how the spray works, and demonstrating how the spray works.

More particularly, the safety of the composition, device and method is reviewed, typically including a recommendation to keep eyes closed when spraying above the nostrils as an added safety level. Any eye, inhalation, grounding/electrical safety or other concerns which the user may have are addressed.

How the spray works is generally explained, for example, by explaining that the product is a fine mist of product droplets that are charged so that they stay separated during application and are uniquely attracted to the face versus non-target areas such as the hair, clothing, etc., yet needs no blending.

Demonstrating how the spray works preferably includes showing how to hold the device (e.g., by resting it between the thumb and fore finger), and how to activate the device (e.g., by pressing the on/off button with your fore-finger, preferably instructing to keep fingers away from the nozzle). A useful demonstration before actual use involves providing a visible expectation (i.e., how the product comes out of the device), e.g., by spraying on a piece of paper, paper towel, non-target skin (e.g, hand or arm) or the like, and providing a tactile expectation, e.g., by spraying on non-target skin to show how the spray feels on the skin. The user should understand that the product is emitted as a fine, uniform spray or mist that needs no blending into the skin, which is very light in feel. The user should also preferably understand that the mist generally forms a circular, versus linear (jets) pattern and that the swath diameter is proportional to the distance of the device from the face.

Other means may be provided to enhance the user's experience, e.g., music or other audio effects, flowers, aromatherapy, massage, or other known means of promoting relaxation.

c) Self-application Training

Where the user intends to self-apply the product, the learning curve for self-applying the composition is also important to user satisfaction. Preferred training involves at least a step of joint application by the user and a second party. More preferred training methods allow the user to gradually become familiar with the techniques, and involve a sequence of steps comprising application by a second party, joint application by the user and a second party, and full application by the user with optional assistance of a second party or instructional materials. The steps are preferably performed on different days, more preferably on consecutive days. However, the steps may be performed on the same day and optionally immediately following each other if it is practical and provided that cleansing of the user's skin between steps does not cause negative effects.

One preferred method of training is a 3–5 day training period during which the user gradually becomes comfortable with self-application:

(1) On the first day, a second party applies the product to the end-user.
(2) On the second day, the second party applies product to half the end-user's face and then the end-user completes the application with personalized guidance from the second party and/or instructional aids such as a usage pamphlet and/or a video of others self-applying the product. The second party or instructional aid preferably reminds the end user of the proper device distance, speed, the desirability of keeping the eyes closed as described above, and other helpful suggestions such as described above, e.g., such as beginning with the jaw line and working "up" the face until becoming more comfortable with the application process.
(3) On the third day, the end-user applies full face product with optional guidance from the second party and/or instructional materials.
(4) On optional fourth and fifth days, the third day procedure is repeated.

When it is desirable to demonstrate self-application with a single demonstration, the preferred method is to follow the above instructions for the second day.

The self-application learning curve preferably involves three elements of expectation or context, technique or application, and confidence. Expectation/context involves addressing any safety concerns and describing the product which comes out of the device. Technique/application involves application techniques, including how to hold/handle the device and instructions regarding proper distance from the face, amount of product to apply, how long to apply, hand motion, and application speeds. Confidence involves allowing the user to practice applying the product, optionally with assistance from a second party or other instructional aids. Preferred aspects of these elements is as described herein above.

(C) Other Topical Application Methods

The topical compositions can alternatively be applied to the skin to form the discontinuous films by silk screen techniques or the like, and additionally by using application techniques which provide product deposition via the use of normal forces (i.e., forces perpendicular to skin surface).

In the first method, a piece of plastic, metal, cloth or other mesh (preferably conformable to facial contours), with evenly spaced holes/pores of about 150 microns or less in diameter is placed against the skin. Then topical composition, e.g., a pigmented foundation, is pressed through the holes in the mesh to deposit the same pattern of droplets on the skin which exists in the pores of the mesh. One convenient way to press the fluid through the mesh is to first absorb it into a sponge, cloth or other absorbent material and then to press the soaked sponge or other material against the mesh. Another means of accomplishing this is to spread or draw the fluid across the mesh with a stiff-edged product such as a rubber squeegee, much like spackling a wall. After the product is pressed through the mesh, the mesh is removed, and cleaned if desired for re-use. The mesh is then moved to any bordering, uncovered areas and the process is repeated as many times as necessary to complete application of the target area. Once the fluid on the skin has dried, if applicable, the process may be repeated by placing the mesh back over the areas where product is already deposited, and orienting the mesh at a different angle to minimize the potential for overlapping droplets. This re-application process will allow for tighter particle spacing than inherently exists in the mesh, if desired.

Any type mesh which allows for a deposition with the desirable size and spacing pattern described herein may be used. Examples of such materials include microaperatured formed films as are described in U.S. Pat. No. 4,342,314, issued to Radel et al. on Aug. 3, 1982 and U.S. Pat. No. 4,629,643 issued to Curro et al. on Dec. 16, 1986, both of which are herein incorporated by reference in their entirety. As is described in these references, suitable materials for these formed films are preferably polyolefins, e.g., polyester. Preferable mesh hole size and spacing is equivalent to the desired end discontinuous film particle size and spacing.

Alternatively, the discontinuous deposition pattern is achieved without the use of a mesh or screen, but rather is accomplished through the use of a porous material with pores which are less than about 150 microns in diameter. The porous structure may comprise open cells, closed cells, or some combination thereof. The term "cells", as used herein, refers to the 3-dimensional voids present in the material which may, or may not have interstitial openings which would connect the voids to one another. In one embodiment, the fluid topical skin product is absorbed into the porous material and then "blotted" onto the skin using forces perpendicular to the skin (as opposed to tangential, or shearing forces). This application technique uses the pore size and pore spacing of the material to create the discontinuous deposition pattern.

Such porous materials can be created by techniques which include, but are not limited to:

1) seeding mechanisms in which the pores are created by incorporating a physical material which is later extracted, destroyed, removed, or decays after the structure is formed, examples of such materials include elastomeric rubber structures manufactured by the Porelon and MicroFoam Companies such as Porlon and Microfoam brand materials which are described in U.S. Pats. No. 3,971,315 and 4,824,621, both of which are herein incorporated by reference in their entirety;

2) aerating (i.e., incorporating air or inert gases into) polymeric materials via mechanical shearing, high pressure (e.g., forced air), or the like, examples include foams of synthetic latex nitrites produced Latex Foam Products, Inc. (LFP) such as "NBR", "SBR", or "SK" type materials;

3) using emulsion chemistry and processing techniques to control the pore size and density—examples of such materials include polyurethane foams produced by the Lendell corporation, or flexible microcellular foams such as those cited in U.S. Pat. No. 5,260,345 and 4,522,953, both of which are herein incorporated by reference in their entirety.

4) sintering powder particulates of various sizes to create the desired pore size and density—examples of such materials which utilize particulates of high density polyethylene, polypropylene, or nylon and are produced by the Porex Technologies Corporation (e.g. Porex X4900 and X4800 series in coarse sheets or custom-molded parts).

In another variation on the use of porous materials to create a discontinuous pattern, a continuous or discontinuous film of fluid is applied to the skin and the porous material (as described above) is subsequently blotted onto the continuous film to remove fluid from the skin surface by absorbing the fluid into the pores of the material. The discontinuous pattern, in this case, is formed by and corresponds to the structural pattern of the polymeric material which separates the pores. In this example, the spacing of polymeric material which separates the pores should be less than 150 microns in effective diameter. The phrase "effective diameter", as used herein, refers to the diameter of a circle with an area equal to the area of the irregularly shaped region of interest.

In yet another execution, the discontinuous pattern is created by blotting non-porous materials with a relief texture in which the raised areas of the texture do not exceed 150 microns in effective diameter. In this execution the nonporous, textured material is blotted into a fluid reservoir (much like an ink pad), imparting the fluid product onto the raised textured areas of the non-porous substrate. The substrate is then blotted onto the skin (using forces normal to the skin) and the raised textured pattern of the nonporous material is transferred to the skin surface.

In still another execution, the discontinuous pattern is created by blotting non-porous materials with a relief texture where the reliefed areas of the texture do not exceed 150 microns in effective diameter. The phrase relief texture or reliefed areas, as used herein, refers to the depressed areas of the textured surface or textures formed by such depressed areas or regions. In this execution the nonporous, textured material is blotted into a fluid reservoir, imparting the fluid product onto all surfaces of the substrate (both raised and depressed). The fluid product on the raised areas is then removed through a secondary process such wiping, absorbing, evaporating, or the like. The substrate is then blotted onto the skin (using forces normal to the skin) and the depressed textured pattern of the nonporous material is transferred to the skin surface.

(IV) EXAMPLES

The following examples illustrate the present invention but are not intended to be limiting thereof:

Examples 1–5

Cosmetic foundations are made by combining the following ingredients:

| Ingredient | Ex 1 | Ex 2 | Ex 3 | Ex 4 | Ex 5 |
|---|---|---|---|---|---|
| Group A: | | | | | |
| Cyclomethicone 245 | 15.22 | 15.81 | 17.9 | 15.22 | 13.22 |
| Cyclomethicone & Dimethicone Copolyol | 10.40 | 11.46 | 10.74 | 10.40 | 10.40 |
| Cetyl Dimethicone Copolymer | 0.50 | 0.50 | 0.52 | 0.5 | 0.5 |
| Group B: | | | | | |
| Titanium Dioxide - Dimethicone Treated | 5.35 | 12.03 | 5.51 | 5.35 | 5.35 |
| Yellow Iron Oxide | 0.64 | 2.45 | 0.65 | 0.64 | 0.64 |
| Red Iron Oxide | 0.13 | 0.50 | 0.14 | 0.13 | 0.13 |
| Black Iron Oxide | 0.08 | 0.09 | 0.08 | 0.08 | 0.08 |
| Micronized Titanium Dioxide | 0.16 | 0.79 | 0.17 | 0.16 | 0.16 |
| Ethylene Acrylates Copolymer[1] | 3.00 | 3 | 3.09 | 3 | 3 |
| Boron Nitride UHP 11072[2] | 3.00 | 3 | 3.09 | 3 | 3 |
| Talc - Dimethicone Treated | 3.03 | 4.37 | 3.13 | 3.02 | 3.02 |
| Group C: | | | | | |
| Organosiloxane resin[3] | 3.00 | 3 | 3 | 3 | 10 |
| Group D: | | | | | |
| Propylene Glycol | 55.50 | 43 | 52 | 55.17 | 50.5 |
| Sodium Chloride | — | — | — | 0.33 | — |

[1]Ethylene Acrylates Copolymer available as EA-209 from Kobo Products.
[2]Boron Nitride UHP 1107 grade available from Carborundum.
[3]MQ Resin (0.7:1 ratio M:Q) available as SR 1000 from General Electric.

Combine the Group A ingredients and mix well with a homogenizer set at 2000–4000 rpm. Add the Group B ingredients. During addition mix at 5000–7500 rpm; when addition is complete set mixing speed to 8000–10000 rpm. Do not let temperature rise above 40 C during mixing. After 30 minutes of mixing check the particle size with a Hegman gauge or glass slides. If the sample has an acceptable particle size (i.e. less than 30 microns). Mix in Part C at a mixing speed of 5000–7500 rpm. Keep temperature in 20 C–40 C range and assist with hand mixing if necessary. After 15 minutes of mixing, raise mixing speed to 7500–10000 rpm. Slowly add Part D ingredients at a rate of 30–40 g/minute, keeping the temperature at 45 C or below (ideally temperature should be from 20–40 C). After addition is complete mix at 5000 rpm–7500 rpm for about 10 minutes. Allow the product to reach ambient conditions and pour into appropriate container.

Examples 6–13

Cosmetic foundations are made by combining the following ingredients:

| Ingredient | Ex 6 | Ex 7 | Ex 8 | Ex 9 | Ex 10 | Ex 11 | Ex 12 | Ex 13 |
|---|---|---|---|---|---|---|---|---|
| Group A: | | | | | | | | |
| Cyclomethicone 245 | 15.25 | 13.3 | 35.37 | 30.4 | 15 | — | — | — |
| Cyclomethicone & Dimethicone Copolyol | 10.44 | 10.44 | 15.44 | 10.44 | 9 | — | — | — |
| Cetyl Dimethicone Copolymer | 0.50 | 0.50 | 0.50 | 0.50 | — | — | — | — |
| Isododecane | — | — | — | — | — | 24.25 | 21.69 | 29.65 |
| Arlacel P135 surfactant (ICI) | — | — | — | — | — | 4.75 | 4.5 | 4.5 |
| Group B: | | | | | | | | |
| Titanium Dioxide - Dimethicone Treated | 5.35 | 5.35 | 5.35 | 5.35 | — | — | 5.35 | 5.35 |
| Yellow Iron Oxide | 0.9 | 0.9 | 0.9 | 0.9 | 0.19 | 0.19 | 0.9 | 0.9 |
| Red Iron Oxide | 0.18 | 0.18 | 0.18 | 0.18 | 1.24 | 1.24 | 0.18 | 0.18 |

-continued

| Ingredient | Ex 6 | Ex 7 | Ex 8 | Ex 9 | Ex 10 | Ex 11 | Ex 12 | Ex 13 |
|---|---|---|---|---|---|---|---|---|
| Black Iron Oxide | 0.05 | 0.05 | 0.05 | 0.05 | — | — | 0.05 | 0.05 |
| Micronized Titanium Dioxide | 0.16 | 0.16 | 0.16 | 0.16 | — | — | 0.16 | 0.16 |
| Ethylene Acrylates Copolymer[1] | 2.94 | 2.96 | 2.94 | 2.94 | 6 | 6 | 2.94 | 2.94 |
| Boron Nitride UHP 11072[2] | 2.94 | 2.94 | 2.95 | 2.94 | 6 | 6 | 2.94 | 2.94 |
| Talc - Dimethicone Treated | 1.33 | 0.95 | 1.22 | 1.21 | — | — | 1.33 | 1.33 |
| Red #7 Ca lake | — | — | — | — | 0.87 | 0.87 | — | — |
| Red #6 Ba lake | — | — | — | — | 0.52 | 0.52 | — | — |
| Blue #1 Al lake | — | — | — | — | 0.24 | 0.24 | — | — |
| Group C: | | | | | | | | |
| Organosiloxane resin[3] | 2.94 | 2.94 | 2.94 | 2.93 | 2.94 | 2.94 | 2.96 | — |
| Group D: | | | | | | | | |
| Compritol 888 ATO (glyceryl behenate) | 2 | — | 2 | 2 | 3 | 3 | 2 | 2 |
| Dow Corning 9040 silicone gel thickener | — | 9.33 | — | — | — | — | — | — |
| Group E: | | | | | | | | |
| Propylene Glycol | 55 | 50 | 30 | 40 | 55 | 50 | 55 | 50 |

[1]Ethylene Acrylates Copolymer available as EA-209 from Kobo Products.
[2]Boron Nitride UHP 1107 grade available from Carborundum.
[3]MQ Resin (0.7:1 ratio M:Q) available as SR 1000 from General Electric.

Combine Group A ingredients and mix well with a homogenizer set at 2000–4000 rpm. Add Group B ingredients. During addition mix at 5000–7500 rpm; when addition is complete set mixing speed to 8000–10000 rpm. Do not let temperature rise above 40 C during mixing. After 30 minutes of mixing check particle size with Hegman gauge or glass slides. If the sample has an acceptable particle size (i.e. less than 30 microns), raise mixing speed to 7500–10000 rpm. Slowly add Part C. After 15 minutes of mixing at 5000–7500 rpm, raise the temperature slowly to 35–40 C. When the temperature has equilibrated, slowly add Part D. The mixing speed should be 5000–7500 rpm for 10 minutes. Slowly decrease temperature to 20 C–35 C, then raise mixing speed to 7500–10000 rpm. Add Part E at approximately 30–40 g/min, keeping the temperature at 45 C or less (ideally temperature should be from 20–40 C). After addition is complete mix at 5000 rpm–7500 rpm for about 10 minutes. Allow to reach ambient conditions and pour into appropriate container, Example 14

A cosmetic blush is made by combining the following ingredients:

| Ingredient | Ex 14 |
|---|---|
| Group A: | |
| Cyclomethicone 245 | 19.89 |
| Cyclomethicone & Dimethicone Copolyol | 10.44 |
| Cetyl Dimethicone Copolymer | 0.50 |
| Group B: | |
| Ethylene Acrylates Copolymer[1] | 2.94 |
| Boron Nitride UHP 11072[2] | 2.96 |
| Talc - Dimethicone Treated | 1.33 |
| Red 6 Ca Lake | 2 |
| Group C: | |
| Organosiloxane resin[3] | 2.94 |

-continued

| Ingredient | Ex 14 |
|---|---|
| Group D: | |
| Compritol 888 ATO (glyceryl behenate) | 2 |
| Group E: | |
| Propylene Glycol | 55 |

[1]Ethylene Acrylates Copolymer available as EA-209 from Kobo Products.
[2]Boron Nitride UHP 1107 grade available from Carborundum.
[3]MQ Resin (0.7:1 ratio M:Q) available as SR 1000 from General Electric.

Prepare as for Examples 6–13.

Example 15

A spray useful for reducing or preventing skin shine is made by combining the following ingredients:

| Ingredient | Ex 15 |
|---|---|
| Group A: | |
| Cyclomethicone 245 | 21.89 |
| Cyclomethicone & Dimethicone Copolyol | 10.44 |
| Cetyl Dimethicone Copolymer | 0.50 |
| Group B: | |
| Ethylene Acrylates Copolymer[1] | 2.94 |
| Boron Nitride UHP 11072[2] | 2.94 |
| Talc - Dimethicone Treated | 1.33 |
| Group C: | |
| Organosiloxane resin[3] | 2.96 |
| Group D: | |
| Compritol 888 ATO (glyceryl behenate) | 2 |

-continued

| Ingredient | Ex 15 |
|---|---|
| Group E: | |
| Propylene Glycol | 55 |

[1] Ethylene Acrylates Copolymer available as EA-209 from Kobo Products.
[2] Boron Nitride UHP 1107 grade available from Carborundum.
[3] MQ Resin (0.7:1 ratio M:Q) available as SR 1000 from General Electric.

Prepare as for Examples 6–13.

Example 16

A topical composition for improving skin texture (e.g., reducing the visibility of lines, wrinkles) is made by combining the following ingredients:

| Ingredient | Ex 16 |
|---|---|
| Group A: | |
| isododecane | 28 |
| Arlacel P135 surfactant | 4.75 |
| Group B: | |
| Coslin C-100 (Englehard) | 4 |
| Group C: | |
| Organosiloxane resin[1] | 3.00 |
| Group D: | |
| Propylene Glycol | 60.25 |

[1] MQ Resin (0.7:1 ratio M:Q) available as SR 1000 from General Electric.

Prepare as for Examples 1–5.

Examples 17–18

Cosmetic foundations are made by combining the following ingredients:

| Ingredient | Ex 17 Wt % | Ex 18 Wt % |
|---|---|---|
| Group A | | |
| Cyclomethicone 245 | 8.59 | 24.26 |
| Cyclomethicone & Dimethicone Copolyol | 11.61 | 12.66 |
| Cetyl Dimethicone Copolymer | 0.30 | 0.36 |
| Group B | | |
| Titanium Dioxide - Dimethicone Treated | 12.52 | 7.34 |
| Yellow Iron Oxide | 2.42 | 1.41 |
| Red Iron Oxide | 0.76 | 0.45 |
| Black Iron Oxide | 0.33 | 0.20 |
| Micronized Titanium Dioxide | 0.38 | 0.23 |
| Talc - Dimethicone Treated | 4.54 | 2.66 |
| Group C | | |
| Synthetic Wax PT-0602 | 0.15 | 0.18 |
| Arachidyl Behenate | 0.46 | 0.53 |
| Silica P-1500 | 0.15 | 0.06 |
| Group D | | |
| Aluminum Starch Octenylsuccinate[1] | 3.79 | 1.49 |
| SPCAT 12 | 0.76 | 0.30 |

-continued

| Ingredient | Ex 17 Wt % | Ex 18 Wt % |
|---|---|---|
| Group E | | |
| Cyclomethicone & Dimethicone Copolyol | 22.54 | 26.40 |
| Silicone 350 cSt Fluid | 3.04 | 3.56 |
| Silicone 50 cSt Fluid | 4.55 | 5.34 |
| Group F | | |
| Trihydroxystearin | 0.46 | 0.53 |
| Cyclomethicone 245 | 1.52 | 1.78 |
| Laureth-7 | 0.76 | 0.19 |
| Propylparaben | 0.38 | 0.09 |
| Group G | | |
| Ethanol | 20.00 | 5.00 |
| lecithin | — | 5.00 |

[1] Aluminum Starch Octenylsuccinate availabie as Dry Flo from National Starch.

Combine Group A ingredients and mix well with a homogenizer set at 2000–4000 rpm. Add Group B ingredients. During addition mix at 5000–7500 rpm; when addition is complete set mixing speed to 8000–10000 rpm. Heat batch to 75 C–85 C during mixing. After 30 minutes of mixing check particle size with Hegman gauge or glass slides. If the sample has an acceptable particle size (i.e. less than 30 microns), mix in Part C at a mixing speed of 5000–7500 rpm. Keep Temperature in 75 C–85 C window and assist with hand mixing if necessary. When batch appears uniform, mill at a mixing speed of 8000–10000 rpm for 5 minutes. Add Group D and mix in at a speed of 5000–7500 rpm for 5–10 minutes, assisting with hand mixing if necessary. Add Group E and mix at 5000–7500 rpm for 10 minutes. Adjust temperature to 50–65 C window.

While Groups A–E are being batched, premix Trihydroxystearin in Cyclomethicone 245 at room temperature until lump free. Also premix Propylparaben in Laureth-7 at room temperature until lump free. Ensure batch (Groups A–E) is at 50–65 C, then add premixes. Mix at 5000–7500 rpm for 15–20 minutes. Keep temperature at 50–65 C When complete, cool to room temperature while mixing at 2000–4000 rpm. Once batch is at room temperature, add Group G. Pour into final container.

Example 19

A cosmetic foundation is made by combining the following ingredients:

| Ingredient | Ex 19 Wt % |
|---|---|
| Group A | |
| Cyclomethicone 245 | 40.58 |
| Group B | |
| Titanium Dioxide - Dimethicone Treated | 5.16 |
| Yellow Iron Oxide | 1.57 |
| Red Iron Oxide | 0.50 |
| Black Iron Oxide | 0.22 |
| Micronized Titanium Dioxide | 0.26 |
| Ethylene Acrylates Copolymer[1] | 5.00 |
| Mearl Mica Treated SVA | 3.00 |
| Talc - Dimethicone Treated | 2.96 |

-continued

| Ingredient | Ex 19 Wt % |
|---|---|
| Group C | |
| Bentone 38 | 5.40 |
| Group D | |
| Silicone 350 cSt Fluid | 7.20 |
| Silicone 50 cSt Fluid | 10.80 |
| Group E | |
| Ethanol | 17.35 |

[1] Ethylene Acrylates Copolymer available as EA-209 from Kobo Products.

Combine Group A ingredients and mix well with a homogenizer set at 2000–4000 rpm. Add Group B ingredients. During addition mix at 5000–7500 rpm, when addition is complete set mixing speed to 8000–10000 rpm. Do not let Temperature rise above 40 C during mixing. After 30 minutes of mixing check particle size with Hegman gauge or glass slides. If the sample has an acceptable particle size (i.e. less than 30 microns), mix in Part C at a mixing speed of 5000–7500 rpm. Keep Temperature in 20 C–40 C window. Assist with hand mixing. After 15 mins of mixing prepare to add Part D. Raise mixing speed to 5000–7500 rpm. Slowly add Part D, keeping the temperature at 45 C or less (ideally temperature should be in 20–40 C window). After addition is complete mix at 5000 rpm–7500 rpm for about 10 minutes. After 10 minutes allow to reach ambient conditions. Add Group E and mix at 5000–7500 rpm for about 15 minutes. Maintain batch at ambient conditions. When complete, pour into final container.

The products of Examples 1–19 are electrostatically sprayed to the face in accordance with the description herein.

Additional wear or transfer resistant products which can be applied, e.g., by silk screen techniques such as described herein to provide films according the invention are described in PCT Application Nos. WO97/17058, published May 15, 1997 and WO96/33689, published Oct. 31, 1996 and U.S. Pat. Nos. 5,800,816 and 5,505,937.

What is claimed is:

1. A discontinuous film deposited onto skin, wherein said film is formed from the deposition onto said skin of an electrostatically sprayed topical cosmetic composition, the composition comprising one or more particulate materials dispersed in a carrier comprising at least one liquid diluent, wherein upon deposition onto said skin the film has an average particle size of from about 0.5 to about 150 microns, an average spacing between particles of at least about 3 microns, and a coverage value of about 80% or less.

2. The film of claim 1 wherein the average particle size is from about 1 to about 100 microns.

3. The film of claim 1 wherein the average particle size is from about 5 to about 80 microns.

4. The film of claim 1 wherein the average spacing between particles is at least about 7 microns.

5. The film of claim 1 wherein the average spacing between particles is at least about 10 microns.

6. The film of claim 1 wherein the standard deviation for the average particle size is less than about 1.5 times the average particle size.

7. The film of claim 1 wherein the standard deviation for the average particle size is less than about 1.0 times the average particle size.

8. The film of claim 1 wherein the standard deviation for the average particle size is less than about 0.7 times the average particle size.

9. The film of claim 1 wherein the coverage value is less than about 70%.

10. The film of claim 1 wherein the coverage value is less than about 60%.

11. The film of claim 1 wherein the film is formed by passing the topical composition through a mesh.

12. The film of claim 1 wherein the topical cosmetic composition is a cosmetic foundation.

* * * * *